United States Patent
Jiang et al.

(10) Patent No.: US 12,115,160 B2
(45) Date of Patent: *Oct. 15, 2024

(54) COMBINED USE OF IN10018 AND PLD

(71) Applicant: INXMED (NANJING) CO., LTD., Nanjing (CN)

(72) Inventors: Jun Jiang, Beijing (CN); Shuang Xie, Beijing (CN); Jiangwei Zhang, Shanghai (CN); Zaiqi Wang, Shanghai (CN)

(73) Assignee: INXMED (NANJING) CO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/454,922

(22) Filed: Aug. 24, 2023

(65) Prior Publication Data

US 2023/0390289 A1 Dec. 7, 2023

Related U.S. Application Data

(63) Continuation of application No. PCT/CN2022/110234, filed on Aug. 4, 2022.

(30) Foreign Application Priority Data

Aug. 16, 2021 (CN) .......................... 202110935854.9

(51) Int. Cl.
*A61K 31/506* (2006.01)
*A61K 31/704* (2006.01)
*A61P 35/00* (2006.01)

(52) U.S. Cl.
CPC .......... *A61K 31/506* (2013.01); *A61K 31/704* (2013.01); *A61P 35/00* (2018.01)

(58) Field of Classification Search
CPC ...... A61K 31/506; A61K 31/704; A61P 35/00
USPC ...................................................... 514/275
See application file for complete search history.

(56) References Cited

U.S. PATENT DOCUMENTS

| | | |
|---|---|---|
| 8,846,689 B2 | 9/2014 | Stadtmueller et al. |
| 2016/0264574 A1 | 9/2016 | Stogniew et al. |
| 2016/0346282 A1 | 12/2016 | Pachter et al. |
| 2018/0177788 A1 | 6/2018 | Pachter et al. |
| 2023/0000867 A1 | 1/2023 | Wang et al. |
| 2023/0145356 A1 | 5/2023 | Wang et al. |
| 2023/0364088 A1 | 11/2023 | Wang et al. |
| 2024/0024319 A1 | 1/2024 | Wang et al. |

FOREIGN PATENT DOCUMENTS

| | | |
|---|---|---|
| CA | 3125058 A1 | 7/2020 |
| CN | 102292322 A | 12/2011 |
| CN | 108289892 A | 7/2018 |
| CN | 111565742 A | 8/2020 |
| EP | 4101453 A1 | 12/2022 |
| WO | 2010058032 A2 | 5/2010 |
| WO | 2012136829 A1 | 10/2012 |
| WO | 2015120289 A1 | 8/2015 |
| WO | 2017004192 A1 | 1/2017 |
| WO | WO-2020202005 A1 * | 10/2020 ........... A61K 31/337 |
| WO | 2021048339 A1 | 3/2021 |
| WO | 2021104454 A1 | 6/2021 |
| WO | 2021154929 A1 | 8/2021 |
| WO | WO-2021155764 A1 * | 8/2021 ........... A61K 31/337 |

OTHER PUBLICATIONS

Li et al Journal of Ovarian Research, 2021, 14:42, 1-12 (Year: 2021).*
Mohanty et al Expert Opinion on Investigational Drugs, 2020, 29(4), 399-409 (Year: 2020).*
WO 2021155764 machine translation (Year: 2021).*
Medical Guanian, English translation, https://xueqiu.com/9766314542/137684324 (Year: 2019).*
He et al., "Studies on the Role of Focal Adhesion Kinase in Disease," Acta Neuropharmacologica (2021) vol. 11, No. 3, pp. 50-64. Chinese with English abstract.
Zhang et al., "Focal Adhesion Kinase (FAK) Inhibition Synergizes with Kras G12C Inhibitors in Treating Cancer through the Regulation of the FAK-YAP Signaling," Advanced Science (2021) vol. 8, Article e2100250, 15 pages.

(Continued)

*Primary Examiner* — Yevgeny Valenrod
(74) *Attorney, Agent, or Firm* — K&L Gates LLP

(57) ABSTRACT

The present invention relates to the combined use of: (a) the compound of formula (I) or a pharmaceutically acceptable salt thereof; and (b) PLD or a pharmaceutically acceptable salt thereof, for treating ovarian cancer.

18 Claims, 1 Drawing Sheet

Formula I

(56) References Cited

OTHER PUBLICATIONS

Ferrandina et al., "Phase III Trial of Gemcitabine Compared With Pegylated Liposomal Doxorubicin in Progressive or Recurrent Ovarian Cancer," J Clin Oncol (2008) vol. 26, No. 6, pp. 890-896.

Mutch et al., "Randomized Phase III Trial of Gemcitabine Compared With Pegylated Liposomal Doxorubicin in Patients With Platinum-Resistant Ovarian Cancer," J Clin Oncol (2007) vol. 25, No. 19, pp. 2811-2818.

Doi et al., "Phase I Study of the Focal Adhesion Kinase Inhibitor BI 853520 in Japanese and Taiwanese Patients with Advanced or Metastatic Solid Tumors," Targeted Oncology (2019) vol. 14, pp. 57-65.

[No Author Listed] Press Release—"Congratulations! Yingshi BioFAK inhibitor was approved for clinical use in China," retrieved from xueqiu.com/9766314542/137684324, (2019) 3 pages.

International Search Report issued in PCT/CN2021/074371, mailed on Mar. 30, 2021.

[No Author Listed] Press Release: "Yingshi Biotechnology and MSD have reached a global clinical collaboration to evaluate the combination of FAK inhibitors and parolizumab," Medical Mission/Report, Jan. 7, 2020, retrieved from xueqiu.com/9766314542/138813166, three pages, Chinese with English translation.

[No Author Listed] Press Release: "Yingshi Biological FAK Inhibitor IN10018 Phase I Clinical Trial Approved in China," PR Newswire, Dec. 20, 2019, retrieved from prnasia.com/story/268783-1.shtml, Chinese with English translation.

Laszlo et al., "The FAK inhibitor BI 853520 inhibits spheroid formation and orthotopic tumor growth in malignant pleural mesothelioma," Journal of Molecular Medicine (2019) vol. 97, pp. 231-242.

Solomon et al., "Clinical Pharmacology of Liposomal Anthacyclines: Focus on Pegylated Liposomal Doxorubicin," Clinical Lyphoma & Myeloma (2008) vol. 8, No. 1, pp. 21-32.

Gupta et al., "Salts of Therapeutic Agents: Chemical, Physicochemical, and Biological Considerations," Molecules (2018) vol. 23, Article 1719, 15 pages.

[No Author Listed] "Congratulations! Instec Fak inhibitors are clinically approved in China," Press release, Medicine Guanlan Report, WuXi AppTec published on Dec. 19, 2019, 3 pages.

Bastin et al., "Salt Selection and Optimization Procedures for Pharmaceutical New Chemical Entities," Organic Process Research & Development (2000) vol. 4, pp. 427-435.

Beierle et al., "TAE226 inhibits human neuroblastoma cell survival," Cancer Investigation (2008) vol. 26, pp. 145.151.

Cuiffo et al., "Palmitoylation of oncogenic NRAS is essential for leukemogenesis," Blood (2010) vol. 115, No. 17, pp. 3598-3605.

Dragoj et al., "Targeting CXCR4 and FAK reverses doxorubicin resistance and suppresses invasion in non-small cell lung carcinoma," Cell Oncol (2017) vol. 40, pp. 47-62.

Fredericks et al., "The role of RAS effectors in BCR/ABL induced chronic myelogenous leukemia," Front Med (2013) vol. 7, No. 4, pp. 452-461.

Golubovskaya et al., "Disruption of focal adhesion kinase and p53 interaction with small molecule compound R2 reactivated p53 and blocked tumor growth," BMC Cancer (2013) vol. 13, Article 342, 14 pages.

Golubovskaya et al., "MiR-138 and MiR-135 Directly Target Focal Adhesion Kinase, Inhibit Cell Invasion , and Increase Sensitivity to Chemotherapy in Cancer Cells," Anticancer Agents Med Chem (2014) vol. 14, No. 1, pp. 18-28.

Hirata et al., "Intravital Imaging Reveals How BRAF Inhibition Generates Drug-Tolerant Microenvironments with High Integrin Beta1/FAK Signaling," Cancer Cell (2015) vol. 27, pp. 574-588.

Hirt et al., "Efficacy of the highly selective focal adhesion kinase inhibitor BI 853520 in adenocarcinoma xenograft models is linked to a mesenchymal tumor phenotype," Oncogenesis (2018) vol. 7, Article 21, 11 pages.

International Search Report and Written Opinion issued in PCT/CN2020/129350, mailed Feb. 22, 2021, Chinese with English translation.

Kurenova et al., "A Fak scaffold inhibitor disrupts FAK and VEGFR-3 signaling and blocks melanoma growth by targeting both tumor and endothelial cells," Cell Cycle (2014) vol. 13, Iss. 16, pp. 2542-2533.

Kurenova et al., "The Small Molecule Chloropyramine Hydrochloride (C4) Targets the Binding Site of Focal Adhesion Kinase and Vascular Endothelial Growth Factor Receptor 3 and Suppresses Breast Cancer Growth in vivo," J Med Chem (2009) vol. 52, No. 15, pp. 4716-4724.

Lee et al., "FAK signaling in human cancer as a target for therapeutics," Pharmacology & Therapeutics (2015) vol. 146, pp. 132-149.

Parikh et al., "Oncogenic NRAS, KRAS, and HRAS Exhibit Different Leukemogenic Potentials in Mice," Cancer Res (2007) vol. 67, No. 15, pp. 7139-7146.

Signorelli et al., "Cobimetinib: A Novel MEK Inhibitor for Metastatic Melanoma," Annals of Pharmacotherapy (2017) vol. 51, No. 2, pp. 146-153.

Tavora et al., "Endothelial-cell FAK targeting sensitizes tunours to DNA-damaging therapy," Nature (2014) vol. 514, pp. 112-116 and Methods pages.

Tiede et al., "The FAK inhibitor BI 853520 exerts anti-tumor effects in breast cancer," Oncogenesis (2018) vol. 7, Article 73, 19 pages.

Yu et al., "Connexin 32 affects doxorubicin resistance in hepatocellular carcinoma cells mediated by Src/FAK signaling pathway," Biomedicine & Pharmacotherapy (2017) vol. 95, pp. 1844-1852.

Zhang et al., "A Simple Statistical Parameter for Use in Evaluation and Validation of High Throughput Screening Assays," Journal of Biomolecular Screening (1999) vol. 4, No. 2, pp. 67-73.

Zhang et al., "Bcr-Abl Efficiently Induces a Myeloproliferative Disease and Production of Excess Interleukin-3 and Granulocyte-Macrophase Colony-Stimulating Factor in Mice: A Novel Model for Chronic Myelogenous Leukemia," Blood (1998) vol. 92, No. 10, pp. 3829-3840.

Zhang et al., "Efficacy of focal adhesion kinase inhibition in non-small cell lung cancer with oncogenically activated MAPK pathways," British Journal of Cancer (2016) vol. 115, pp. 203-211.

Zhang et al., "Gain-of-Function RHOA Mutatations Promote Focal Adhesion Kinase Activation and Dependency in Diffuse Gastric Cancer," Cancer Discovery (2020) vol. 10, pp. 288-305.

De Jonge et al., "Phase I Study of BI 853520, an Inhibitor of Focal Adhesion Kinase, in Patients with Advanced or Metastatic Nonhematologic Malignancies," Targeted Oncology (2019) vol. 14, pp. 43-55.

\* cited by examiner

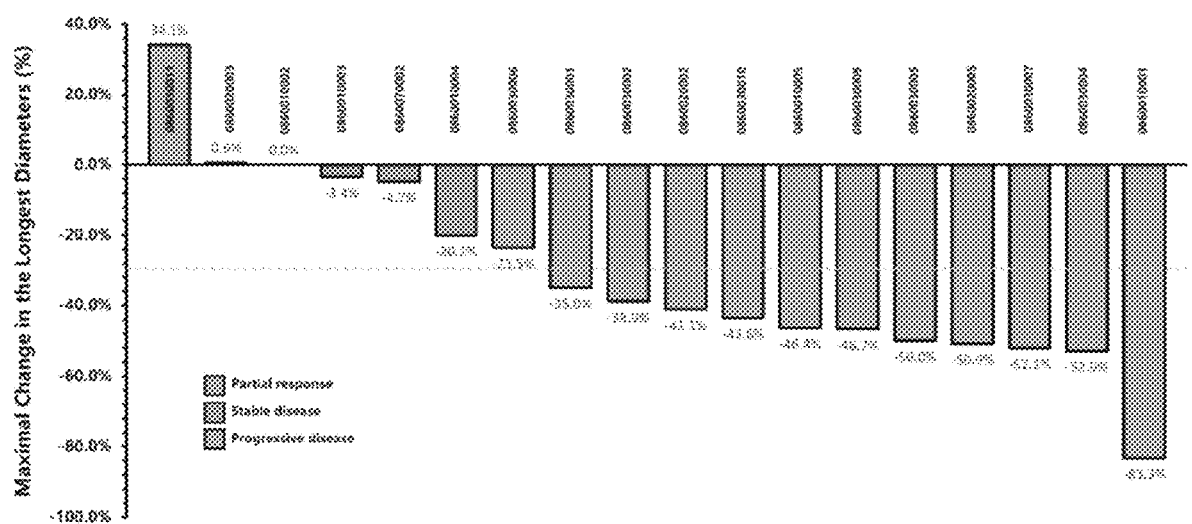

COMBINED USE OF IN10018 AND PLD

This application is a national application filed under 35 U.S.C. 111(a) of PCT/CN2022/110234, filed Aug. 4, 2022, which claims the priority of the Chinese Patent Application No. 202110935854.9 filed on Aug. 16, 2021. The above-identified applications are incorporated herein by reference as part of the disclosure of the present application.

FIELD OF THE INVENTION

The present disclosure belongs to the field of pharmaceutical chemistry. Particularly, the present disclosure relates to the combined use of IN10018 or a pharmaceutically acceptable salt thereof and PLD or a pharmaceutically acceptable salt thereof for treating or preventing ovarian cancer.

BACKGROUND OF THE INVENTION

Cancer is one of the most serious diseases that threaten human life and health. Seven million people die from cancer worldwide every year. At present, there are four main methods of cancer treatment: surgery, drug therapy, radiation therapy and immunotherapy, in addition to adjuvant therapy. Among them, the drug therapy of cancer includes targeted drug therapy and chemotherapy. Among the current treatment methods, targeted drug therapy and chemotherapy still occupy an important position and are important standard therapies for cancer.

Ovarian cancer has the third highest incidence rate among female reproductive organ malignant tumors, which is only lower than that of cervical cancer and endometrial carcinoma. However, among these three diseases, early clinical diagnosis of ovarian cancer is the most difficult, with 70% of ovarian cancer patients already at the advanced stage of the disease by the time they are diagnosed. Thus, the mortality rate of ovarian cancer ranks first among malignant tumors of female reproductive organs. The combined chemotherapy of carboplatin/paclitaxel is the first-line treatment regimen for ovarian cancer. However, the biggest problem of targeted drug therapy and chemotherapeutic drug monotherapy is drug resistance, including spontaneous drug resistance and adaptive drug resistance, which results in a low overall remission rate and a limited duration of remission.

Therefore, finding a way to improve the efficacy of single drug in chemotherapy and to further overcome the problem of drug resistance is an urgent technical challenge in the current cancer treatment.

SUMMARY OF THE INVENTION

The compound of formula (I) herein, i.e. compound IN10018, is 2-fluoro-5-methoxy-4-[(4-(2-methyl-3-oxo-2,3-dihydro-1H-isoindole-4-oxy)-5-trifluoromethyl-pyrimidin-2-yl)amino]-N-(1-methyl-piperidin-4-yl)benzamide (see WO2010058032, which is incorporated herein by reference in its entirety), the compound having the following structure:

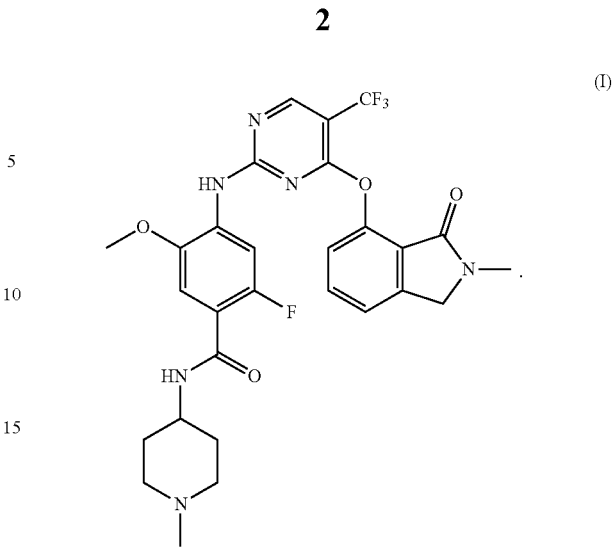

"PLD" herein refers to pegylated liposomal doxorubicin, also known as doxorubicin liposome.

In one aspect, the present invention provides a method of treating or preventing ovarian cancer which comprises administering to a subject in need thereof a therapeutically effective amount of therapeutic agent (a) and therapeutic agent (b), wherein: the therapeutic agent (a) is the compound of formula (I) or a pharmaceutically acceptable salt thereof

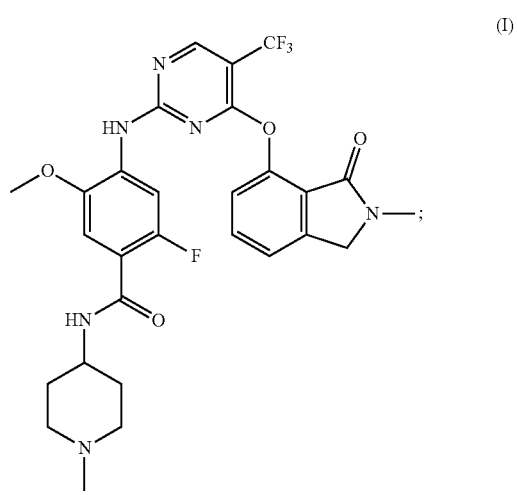

the therapeutic agent (b) is PLD or a pharmaceutically acceptable salt thereof;

the compound of formula (I) or a pharmaceutically acceptable salt thereof is administered at a dose of 10 mg/day to 300 mg/day in an adult; further, the compound of formula (I) or a pharmaceutically acceptable salt thereof is administered at a dose of 25 mg/day to 200 mg/day; furthermore, the compound of formula (I) or a pharmaceutically acceptable salt thereof is administered at a dose of 50 mg/day to 150 mg/day for example at a dose of 100 mg/day in an adult, and the doses are all calculated based on free base.

Optionally, the therapeutic agent (a) and the therapeutic agent (b) in the pharmaceutical combination product are administered simultaneously, separately or sequentially.

Optionally, the PLD or a pharmaceutically acceptable salt thereof is administered at a dose of 20-40 mg/m$^2$ per week preferably at a dose of 40 mg/m² per week in an adult, and the doses are all calculated based on PLD.

Optionally, the pharmaceutically acceptable salt of the compound of formula (I) is tartrate.

Optionally, the compound of formula (I) or a pharmaceutically acceptable salt thereof is administered daily, and PLD or a pharmaceutically acceptable salt thereof is administered once a week, every 4 weeks (28 days) as a cycle.

Optionally, the ovarian cancer is ovarian epithelial cancer.

Optionally, the ovarian epithelial cancer is recurrent ovarian epithelial cancer. Further, the recurrent ovarian epithelial cancer is platinum-resistant recurrent ovarian epithelial cancer or platinum-sensitive recurrent ovarian epithelial cancer. Furthermore, the recurrent ovarian epithelial cancer is platinum-resistant recurrent ovarian epithelial cancer.

In another aspect, the present invention provides use of therapeutic agent (a) and therapeutic agent (b) in the manufacture of a medicament for combined treatment of ovarian cancer, wherein: the therapeutic agent (a) is the compound of formula (I) or a pharmaceutically acceptable salt thereof

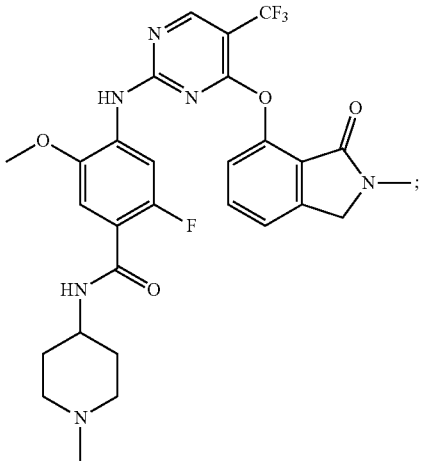

(I)

the therapeutic agent (b) is PLD or a pharmaceutically acceptable salt thereof;
the compound of formula (I) or a pharmaceutically acceptable salt thereof is administered at a dose of 10 mg/day to 300 mg/day in an adult; further, the compound of formula (I) or a pharmaceutically acceptable salt thereof is administered at a dose of 25 mg/day to 200 mg/day in an adult; furthermore, the compound of formula (I) or a pharmaceutically acceptable salt thereof is administered at a dose of 50 mg/day to 150 mg/day for example at a dose of 100 mg/day in an adult, and the doses are all calculated based on free base.

Optionally, the therapeutic agent (a) and the therapeutic agent (b) are administered simultaneously, separately or sequentially.

Optionally, the PLD or a pharmaceutically acceptable salt thereof is administered at a dose of 20-40 mg/m² per week preferably at a dose of 40 mg/m² per week in an adult, and the doses are all calculated based on PLD.

In another aspect, the present invention provides use of therapeutic agent (b) in the manufacture of a medicament for treating ovarian cancer in combination with therapeutic agent (a), wherein: the therapeutic agent (a) is the compound of formula (I) or a pharmaceutically acceptable salt thereof

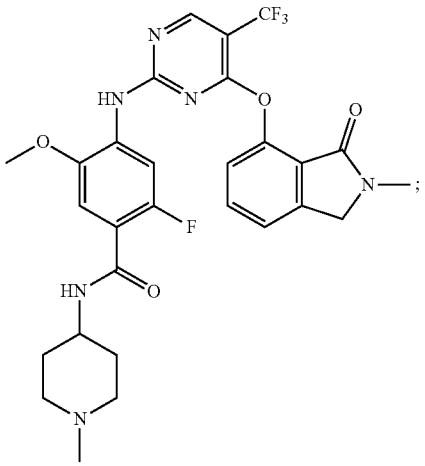

(I)

the therapeutic agent (b) is PLD or a pharmaceutically acceptable salt thereof;
the compound of formula (I) or a pharmaceutically acceptable salt thereof is administered at a dose of 10 mg/day to 300 mg/day in an adult; further, the compound of formula (I) or a pharmaceutically acceptable salt thereof is administered at a dose of 25 mg/day to 200 mg/day in an adult; furthermore, the compound of formula (I) or a pharmaceutically acceptable salt thereof is administered at a dose of 50 mg/day to 150 mg/day for example at a dose of 100 mg/day in an adult, and the doses are all calculated based on free base.

Optionally, the therapeutic agent (a) and the therapeutic agent (b) are administered simultaneously, separately or sequentially.

Optionally, the PLD or a pharmaceutically acceptable salt thereof is administered at a dose of 20-40 mg/m² per week preferably at a dose of 40 mg/m² per week in an adult, and the doses are all calculated based on PLD.

In another aspect, the present invention provides use of therapeutic agent (a) in the manufacture of a medicament for treating ovarian cancer in combination with therapeutic agent (b), wherein: the therapeutic agent (a) is the compound of formula (I) or a pharmaceutically acceptable salt thereof the therapeutic agent (b) is PLD or a pharmaceutically acceptable salt thereof;

the compound of formula (I) or a pharmaceutically acceptable salt thereof is administered at a dose of 10 mg/day to 300 mg/day in an adult; further, the compound of formula (I) or a pharmaceutically acceptable salt thereof is administered at a dose of 25 mg/day to 200 mg/day in an adult; furthermore, the compound of formula (I) or a pharmaceutically acceptable salt thereof is administered at a dose of 50 mg/day to 150 mg/day for example at a dose of 100 mg/day in an adult, and the doses are all calculated based on free base.

Optionally, the therapeutic agent (a) and the therapeutic agent (b) are administered simultaneously, separately or sequentially.

Optionally, the PLD or a pharmaceutically acceptable salt thereof is administered at a dose of 20-40 mg/m² per week preferably at a dose of 40 mg/m² per week in an adult, and the doses are all calculated based on PLD.

In another aspect, the present invention provides therapeutic agent (a) and therapeutic agent (b) for use in the combined treatment of ovarian cancer, wherein: the therapeutic agent (a) is the compound of formula (I) or a pharmaceutically acceptable salt thereof

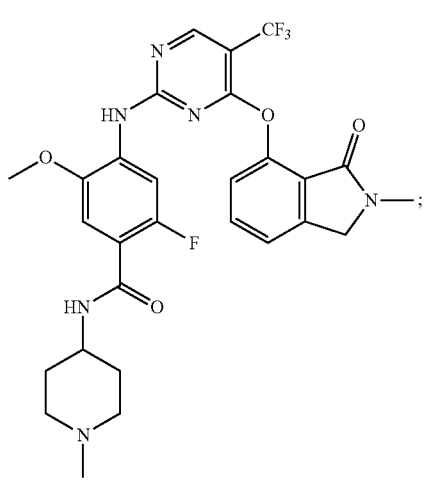

the therapeutic agent (b) is PLD or a pharmaceutically acceptable salt thereof;

the compound of formula (I) or a pharmaceutically acceptable salt thereof is administered at a dose of 10 mg/day to 300 mg/day in an adult; further, the compound of formula (I) or a pharmaceutically acceptable salt thereof is administered at a dose of 25 mg/day to 200 mg/day in an adult; furthermore, the compound of formula (I) or a pharmaceutically acceptable salt thereof is administered at a dose of 50 mg/day to 150 mg/day for example at a dose of 100 mg/day in an adult, and the doses are all calculated based on free base.

In another aspect, the present invention provides therapeutic agent (a) for use in combination with therapeutic agent (b) for treating ovarian cancer, wherein the therapeutic agent (a) is the compound of formula (I) or a pharmaceutically acceptable salt thereof

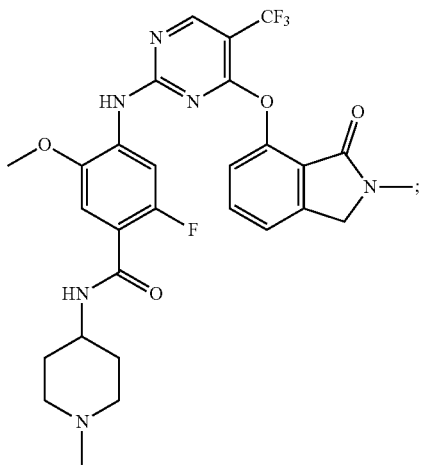

the therapeutic agent (b) is PLD or a pharmaceutically acceptable salt thereof;

the compound of formula (I) or a pharmaceutically acceptable salt thereof is administered at a dose of 10 mg/day to 300 mg/day in an adult; further, the compound of formula (I) or a pharmaceutically acceptable salt thereof is administered at a dose of 25 mg/day to 200 mg/day in an adult; furthermore, the compound of formula (I) or a pharmaceutically acceptable salt thereof is administered at a dose of 50 mg/day to 150 mg/day for example at a dose of 100 mg/day in an adult, and the doses are all calculated based on free base.

In another aspect, the present invention provides therapeutic agent (b) for use in combination with therapeutic agent (a) for treating ovarian cancer, wherein the therapeutic agent (a) is the compound of formula (I) or a pharmaceutically acceptable salt thereof more, the compound of formula (I) or a pharmaceutically acceptable salt thereof is administered at a dose of 50 mg/day to 150 mg/day for example at a dose of 100 mg/day in an adult, and the doses are all calculated based on free base.

Optionally, the therapeutic agent (a) and the therapeutic agent (b) are administered simultaneously, separately or sequentially.

Optionally, the PLD or a pharmaceutically acceptable salt thereof is administered at a dose of 20-40 mg/m² per week preferably at a dose of 40 mg/m² per week in an adult, and the doses are all calculated based on PLD.

Optionally, the pharmaceutically acceptable salt of the compound of formula (I) is tartrate.

Optionally, the compound of formula (I) or a pharmaceutically acceptable salt thereof is administered daily, and PLD or a pharmaceutically acceptable salt thereof is administered once a week, every 4 weeks (28 days) as a cycle.

Optionally, the ovarian cancer is ovarian epithelial cancer.

Optionally, the ovarian epithelial cancer is recurrent ovarian epithelial cancer. Further, the recurrent ovarian epithelial cancer is platinum-resistant recurrent ovarian epithelial cancer or platinum-sensitive recurrent ovarian epithelial cancer. Furthermore, the recurrent ovarian epithelial cancer is platinum-resistant recurrent ovarian epithelial cancer.

In another aspect, the present invention provides a combination formulation comprising (a) a unit dosage form of one or more compounds of formula (I) or a pharmaceutically acceptable salt thereof

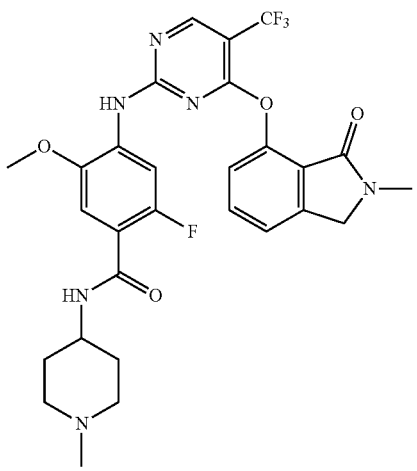

(I)

and (b) a unit dosage form of one or more PLDs or pharmaceutically acceptable salts thereof for the treatment of ovarian cancer.

Optionally, the ovarian cancer is ovarian epithelial cancer.

Optionally, the ovarian epithelial cancer is recurrent ovarian epithelial cancer. Further, the recurrent ovarian epithelial cancer is platinum-resistant recurrent ovarian epithelial cancer or platinum-sensitive recurrent ovarian epithelial cancer. Furthermore, the recurrent ovarian epithelial cancer is platinum-resistant recurrent ovarian epithelial cancer.

BRIEF DESCRIPTION OF THE DRAWINGS

FIG. 1 depicts a waterfall diagram of the best change (%) in the total diameter of target lesions relative to the baseline in the clinical study of treating ovarian cancer by IN10018 combined with PLD.

DETAILED DESCRIPTION OF THE INVENTION

As used herein, the terms "comprise", "contain", and "include" are open-ended expressions that do not exclude other unrecited elements or method steps, but are also understood to include the more restrictive terms "consisting of" and "consisting essentially of".

As used in the specification and appended claims of this application, the terms "a", "an", and "the" and similar expressions are to be construed to encompass both the singular and the plural unless otherwise indicated herein or otherwise clearly contradicted by context.

It will be understood that except in the working examples or where otherwise indicated, all numbers of quantitative properties such as dosages, stated in the specification and claims are to be understood as being modified in all instances by the term "about". It will also be understood that any numerical range recited herein includes all sub-ranges within that range and any combination of endpoints of such ranges or sub-ranges.

As used herein, the term "pharmaceutically acceptable" means non-toxic, biologically tolerable and suitable for administration to a subject.

As used herein, the term "pharmaceutically acceptable salt" refers to a salt that is non-toxic, biologically tolerable and suitable for administration to a subject. The pharmaceutically acceptable salts of the compounds refer to an acid addition salt that is non-toxic, biologically tolerable and suitable for administration to a subject, including but not limited to: acid addition salts formed by the compounds with an inorganic acid, such as hydrochloride, hydrobromide, carbonate, bicarbonate, phosphate, sulfate, sulfite, nitrate, and the like, as well as acid addition salts formed by the compounds with an organic acid, such as formate, acetate, malate, maleate, fumarate, tartrate, succinate, citrate, lactate, methanesulfonate, p-toluenesulfonate, 2-hydroxyethane-sulfonate, benzoate, salicylate, stearate, and salts formed with alkane-dicarboxylic acid of formula HOOC—(CH$_2$)$_n$—COOH (wherein n is 0-4), etc. Pharmaceutically acceptable salts can be obtained by conventional methods well known in the art, for example by reacting a sufficiently basic compound such as an amine with a suitable acid which provides a physiologically acceptable anion. In some embodiments, the pharmaceutically acceptable salt of IN10018 is tartrate.

As used herein, the term the compound of formula (I) generally includes the free base and pharmaceutically acceptable salts thereof unless in the working examples or otherwise indicated or contradicted by context.

The doses disclosed in this application for the compound of formula (I) or a pharmaceutically acceptable salt thereof refer to the doses calculated based on the free base, i.e. the compound of formula (I), unless otherwise indicated.

As used herein, the term PLD generally includes the free base and pharmaceutically acceptable salts thereof unless in the working examples or otherwise indicated or contradicted by context. For instance, examples of acids that can be used to form pharmaceutically acceptable acid addition salts of PLD include inorganic acids such as hydrochloric acid, boric acid, nitric acid, sulfuric acid, and phosphoric acid, as well as organic acids such as formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, p-toluenesulfonic acid and citric acid, and acidic amino acids such as aspartic acid and glutamic acid.

The doses disclosed in this application for PLD or a pharmaceutically acceptable salt thereof refer to doses calculated based on PLD, unless otherwise indicated.

The term "combination" or "pharmaceutical combination" as used herein refers to a product administered in combination as a fixed combination in the form of one dosage unit or a kit-of-parts, wherein therapeutic agents (a) and (b) are administered simultaneously or separately at certain intervals.

The term "pharmaceutical composition" as used herein refers to a mixture or solution comprising at least one therapeutic agent for the prevention or treatment of a particular disease or condition.

An "effective amount" of a combination of therapeutic agents (e.g., the compound of formula (I) and PLD) is an amount sufficient to provide a detectable improvement compared to baseline in clinically observable signs and symptoms of the cancer (e.g., ovarian cancer) being treated by the combination.

The ovarian cancer includes, but is not limited to, ovarian epithelial cancer, which typically includes fallopian tube cancer and primary peritoneal cancer. Recurrent ovarian epithelial cancer is platinum-resistant recurrent ovarian epithelial cancer or platinum-sensitive recurrent ovarian epithelial cancer. Platinum-resistant recurrence in this application means that the interval between the time of discovery of tumor recurrence and the time of the last chemotherapy with previous platinum-containing regimens is less than 6 months or the tumor progresses during initial treatment or relapse treatment. Platinum-sensitive recurrence in this application refers to the interval between the time of discovery of tumor recurrence and the time of the last chemotherapy with previous platinum-containing regimens is at least 6 months.

Paclitaxel chemotherapy drugs include, but are not limited to, paclitaxel, docetaxel, liposomal paclitaxel, albumin-bound paclitaxel, and the like.

Chemotherapy with platinum-containing regimens refers to the use of platinum-based chemotherapy drugs or a combination of platinum-based chemotherapy drugs and other chemotherapy drugs (such as paclitaxel chemotherapy drugs), the platinum-based chemotherapy drugs including but not limited to cisplatin, carboplatin, Nedaplatin, cycloplatin, oxaliplatin, and lobaplatin.

The term "chemotherapy" as used herein refers to a systemic treatment of malignant tumors, which distributes a chemotherapeutic drug into most organs and tissues throughout the body via blood circulation after the chemotherapeutic drug is administered orally, intravenously, or through body cavity. Chemotherapeutic drugs may function at different phases of tumor cell growth and reproduction, inhibiting or killing tumor cells. It is one of the most effective methods for treating malignant tumors.

The terms "combination", "combination therapy" and "combination administration" as used herein refer to using two or more drugs for the treatment of one disease. In some embodiments, the IN10018 or a pharmaceutically acceptable salt thereof is used in combination with a chemotherapeutic drug, for example, PLD or a pharmaceutically acceptable salt thereof, which may further include other drug(s). In some embodiments, the IN10018 or a pharmaceutically acceptable salt thereof and the chemotherapeutic drug for example, PLD or a pharmaceutically acceptable salt thereof, may be administered simultaneously, alternately or sequentially.

The terms "subject" and "patient" used herein are used interchangeably, which refer to mammals and non-mammals. Mammals means any member of the mammalian class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex. In some embodiments, the subject is a human.

The term "treat", "treating" or "treatment" as used herein refers to obtaining a desired pharmacological and/or physiological effect. The effect may be therapeutic and includes partial or substantial achievement of one or more of the following: partial or total reduction in the extent of the disease, condition or syndrome; improvement in clinical symptoms or indicators associated with the disease; or delaying, inhibiting or reducing likelihood of progression of the disease, condition or syndrome.

The term "effective amount" as used herein refers to an amount of the IN10018 (or a pharmaceutically acceptable salt thereof), and the chemotherapeutic drug (such as PLD or a pharmaceutically acceptable salt thereof) sufficient to reduce or ameliorate the severity, duration, progression, or onset of the disease or condition, to delay or arrest the progression of the disease or condition, to cause regression of the disease or condition or delay the recurrence or progression of symptoms, or to enhance or improve the therapeutic effect of another therapy. The precise amount of the IN10018 (or a pharmaceutically acceptable salt thereof) and the chemotherapeutic drug (such as PLD or a pharmaceutically acceptable salt thereof) administered to a subject will depend on various factors, such as the given agent or compound, pharmaceutic preparation, route of administration, the type of disease, the condition, the identity of the subject or host being treated, etc., but can still be routinely determined by those skilled in the art. For example, determination of an effective amount will also depend on the degree, severity, and type of cell proliferation. The skilled artisan will be able to determine the appropriate dosage based on these and other factors. When co-administered with other therapeutic agents, e.g., when co-administered with an anticancer agent, the "effective amount" of any other therapeutic agent will depend on the type of the agent used.

The IN10018 (or a pharmaceutically acceptable salt thereof) can be administered by any suitable method of administration. Suitable methods include oral, intravenous, intramuscular or subcutaneous administration to the subject.

Thus, the IN10018 (or a pharmaceutically acceptable salt thereof) can be administered orally with a pharmaceutically acceptable carrier such as an inert diluent or an absorbable edible carrier. They can be enclosed in hard- or soft-shell gelatin capsules, compressed into tablets, or mixed directly with the patient's food. For oral therapeutic administration, the compound, or a pharmaceutically acceptable salt thereof, can be in combination with one or more excipients and used in a form of ingestible tablets, buccal tablets, lozenges, capsules, elixirs, suspensions, syrups or wafers. These preparations contain an effective amount of the IN10018 (or a pharmaceutically acceptable salt thereof).

Tablets, lozenges, pills, capsules, etc. may further comprise: binders such as tragacanth, acacia, cornstarch or gelatin; excipients such as dicalcium phosphate; disintegrants such as corn starch, potato starch, alginic acid, etc.; lubricants, such as magnesium stearate; or sweeteners, such as sucrose, fructose, lactose or aspartame; or flavoring agents.

The IN10018 (or a pharmaceutically acceptable salt thereof) may also be administered intravenously or intraperitoneally by infusion or injection. Solutions of the IN10018 (or a pharmaceutically acceptable salt thereof) and the chemotherapeutic drug (such as PLD or a pharmaceutically acceptable salt thereof) can be prepared in water, optionally mixed with a nontoxic surfactant.

Exemplary pharmaceutical dosage forms for injection or infusion include: sterile aqueous solutions, dispersions, or sterile powders containing the active ingredient suitable for the extemporaneous preparation of sterile injectable or infusion solutions or dispersions. In any event, the final dosage form should be sterile, fluid, and stable under the conditions of manufacture and storage.

Sterile injectable solutions can be prepared by incorporating a required amount of the IN10018 (or a pharmaceutically acceptable salt thereof) in an appropriate solvent together with other desired ingredients enumerated above and then being filtrated and sterilized. In the case of sterile powders for preparing sterile injectable solutions, the preferred methods of preparation may be vacuum drying and the freeze-drying techniques, which yield a powder of the active ingredient plus any other desired ingredients previously present after sterile filtration.

The amount of the IN10018 (or a pharmaceutically acceptable salt thereof), or the chemotherapeutic drug (such as PLD or a pharmaceutically acceptable salt thereof) may vary not only with the particular salt chosen, but also with the route of administration, the nature of the disease being treated, and the age and condition of the patient, and is ultimately at the discretion of the attending physician or clinician. However, the dosage may generally range from about 0.1 to about 50 mg/kg body weight per day.

The present invention relates to the combined use of IN10018 or a pharmaceutically acceptable salt thereof and PLD or a pharmaceutically acceptable salt thereof for treating or preventing ovarian cancer.

The compound of formula (I) or a pharmaceutically acceptable salt thereof is administered at a dose of 10 mg/day to 300 mg/day in an adult. For example, the compound of formula (I) or a pharmaceutically acceptable salt thereof is administered at a dose of 10 mg/day, 11 mg/day, 12 mg/day, 13 mg/day, 14 mg/day, 15 mg/day, 16 mg/day, 17 mg/day, 18 mg/day, 19 mg/day, 20 mg/day, 21 mg/day, 22 mg/day, 23 mg/day, 24 mg/day, 25 mg/day, 26 mg/day, 27 mg/day, 28 mg/day, 29 mg/day, 30 mg/day, 31 mg/day, 32 mg/day, 33 mg/day, 34 mg/day, 35 mg/day, 36 mg/day, 37 mg/day, 38 mg/day, 39 mg/day, 40 mg/day, 41 mg/day, 42 mg/day, 43 mg/day, 44 mg/day, 45 mg/day, 46 mg/day, 47 mg/day, 48 mg/day, 49 mg/day, 50 mg/day, 51 mg/day, 52 mg/day, 53 mg/day, 54 mg/day, 55 mg/day, 56 mg/day, 57 mg/day, 58 mg/day, 59 mg/day, 60 mg/day, 61 mg/day, 62 mg/day, 63 mg/day, 64 mg/day, 65 mg/day, 66 mg/day, 67 mg/day, 68 mg/day, 69 mg/day, 70 mg/day, 71 mg/day, 72 mg/day, 73 mg/day, 74 mg/day, 75 mg/day, 76 mg/day, 77 mg/day, 78 mg/day, 79 mg/day, 80 mg/day, 81 mg/day, 82 mg/day, 83 mg/day, 84 mg/day, 85 mg/day, 86 mg/day, 87 mg/day, 88 mg/day, 89 mg/day, 90 mg/day, 91 mg/day, 92 mg/day, 93 mg/day, 94 mg/day, 95 mg/day, 96 mg/day, 97 mg/day, 98 mg/day, 99 mg/day, 100 mg/day, 101 mg/day, 102 mg/day, 103 mg/day, 104 mg/day, 105 mg/day, 106 mg/day, 107 mg/day, 108 mg/day, 109 mg/day, 110 mg/day, 111 mg/day, 112 mg/day, 113 mg/day, 114 mg/day, 115 mg/day, 116 mg/day, 117 mg/day, 118 mg/day, 119 mg/day, 120 mg/day, 121 mg/day, 122 mg/day, 123 mg/day, 124 mg/day, 125 mg/day, 126 mg/day, 127 mg/day, 128 mg/day, 129 mg/day, 130 mg/day, 131 mg/day, 132 mg/day, 133 mg/day, 134 mg/day, 135 mg/day, 136 mg/day, 137 mg/day, 138 mg/day, 139 mg/day, 140 mg/day, 141 mg/day, 142 mg/day, 143 mg/day, 144 mg/day, 145 mg/day, 146 mg/day, 147 mg/day, 148 mg/day, 149 mg/day, 150 mg/day, 151 mg/day, 152 mg/day, 153 mg/day, 154 mg/day, 155 mg/day, 156 mg/day, 157 mg/day, 158 mg/day, 159 mg/day, 160 mg/day, 161 mg/day, 162 mg/day, 163 mg/day, 164 mg/day, 165 mg/day, 166 mg/day, 167 mg/day, 168 mg/day, 169 mg/day, 170 mg/day, 171 mg/day, 172 mg/day, 173 mg/day, 174 mg/day, 175 mg/day, 176 mg/day, 177 mg/day, 178 mg/day, 179 mg/day, 180 mg/day, 181 mg/day, 182 mg/day, 183 mg/day, 184 mg/day, 185 mg/day, 186 mg/day, 187 mg/day, 188 mg/day, 189 mg/day, 190 mg/day, 191 mg/day, 192 mg/day, 193 mg/day, 194 mg/day, 195 mg/day, 196 mg/day, 197 mg/day, 198 mg/day, 199 mg/day, 200 mg/day, 201 mg/day, 202 mg/day, 203 mg/day, 204 mg/day, 205 mg/day, 206 mg/day, 207 mg/day, 208 mg/day, 209 mg/day, 210 mg/day, 211 mg/day, 212 mg/day, 213 mg/day, 214 mg/day, 215 mg/day, 216 mg/day, 217 mg/day, 218 mg/day, 219 mg/day, 220 mg/day, 221 mg/day, 222 mg/day, 223 mg/day, 224 mg/day, 225 mg/day, 226 mg/day, 227 mg/day, 228 mg/day, 229 mg/day, 230 mg/day, 231 mg/day, 232 mg/day, 233 mg/day, 234 mg/day, 235 mg/day, 236 mg/day, 237 mg/day, 238 mg/day, 239 mg/day, 240 mg/day, 241 mg/day, 242 mg/day, 243 mg/day, 244 mg/day, 245 mg/day, 246 mg/day, 247 mg/day, 248 mg/day, 249 mg/day, 250 mg/day, 251 mg/day, 252 mg/day, 253 mg/day, 254 mg/day, 255 mg/day, 256 mg/day, 257 mg/day, 258 mg/day, 259 mg/day, 260 mg/day, 261 mg/day, 262 mg/day, 263 mg/day, 264 mg/day, 265 mg/day, 266 mg/day, 267 mg/day, 268 mg/day, 269 mg/day, 270 mg/day, 271 mg/day, 272 mg/day, 273 mg/day, 274 mg/day, 275 mg/day, 276 mg/day, 277 mg/day, 278 mg/day, 279 mg/day, 280 mg/day, 281 mg/day, 282 mg/day, 283 mg/day, 284 mg/day, 285 mg/day, 286 mg/day, 287 mg/day, 288 mg/day, 289 mg/day, 290 mg/day, 291 mg/day, 292 mg/day, 293 mg/day, 294 mg/day, 295 mg/day, 296 mg/day, 297 mg/day, 298 mg/day, 299 mg/day, or 300 mg/day in an adult. In a more specific embodiment, the compound of formula (I) or a pharmaceutically acceptable salt thereof is administered at a dose of 25 mg/day to 200 mg/day in an adult. In a still more specific embodiment, the compound of formula (I) or a pharmaceutically acceptable salt thereof is administered at a dose of 50 mg/day to 150 mg/day in an adult. In an even more specific embodiment, the compound of formula (I) or a pharmaceutically acceptable salt thereof is administered at a dose of 100 mg/day in an adult.

In some embodiments, the PLD is administered at a dose of 20-40 $mg/m^2$ per week in an adult. For example, the PLD is administered at a dose of 20 $mg/m^2$, 21 $mg/m^2$, 22 $mg/m^2$, 23 $mg/m^2$, 24 $mg/m^2$, 25 $mg/m^2$, 26 $mg/m^2$, 27 $mg/m^2$, 28 $mg/m^2$, 29 $mg/m^2$, 30 $mg/m^2$, 31 $mg/m^2$, 32 $mg/m^2$, 33 $mg/m^2$, 34 $mg/m^2$, 35 $mg/m^2$, 36 $mg/m^2$, 37 $mg/m^2$, 38 $mg/m^2$, 39 $mg/m^2$, or 40 $mg/m^2$ per week in an adult. In a preferred embodiment, the PLD is administered at a dose of 40 $mg/m^2$ per week in an adult.

The required dose may conveniently be presented in a single dose or in divided doses administered at appropriate intervals.

The following examples are provided to further illustrate the present disclosure. It should be understood that these examples are only used to illustrate the present disclosure and not to limit the scope of the present disclosure.

The experimental methods without specific conditions in the following examples can be carried out according to the conventional conditions of this type of reaction or according to the conditions suggested by the manufacturers.

The experimental materials and reagents used in the following examples can be obtained from commercial sources unless otherwise specified.

Example 1: Clinical study of IN10018 combined with PLD in the treatment of ovarian cancer IN10018 in combination with pegylated liposomal doxorubicin (PLD) for the treatment of platinum-resistant ovarian cancer is currently being evaluated in a Phase Ib/II clinical study (IN10018-006) in China. The IN10018 was used as its tartrate, and the PLD was used as commercially available doxorubicin hydrochloride liposome injection (common name). Study subjects received IN10018 100 mg once daily (QD) orally combined with PLD 40 mg/m$^2$ by intravenous infusion once every 4 weeks (Q4W). A treatment cycle was 28 days.

By Jul. 30, 2021, a total of 26 patients with platinum-resistant ovarian cancer had been enrolled in the study. All subjects received at least one study drug treatment and were included in the safety analysis; 18 subjects had at least one post-baseline tumor imaging evaluation and were included in efficacy analysis.

The baseline characteristics of the 26 patients with platinum-resistant ovarian cancer enrolled are summarized in Table 1, and the detailed baseline characteristics of the 18 patients with evaluable efficacy are shown in Table 2.

TABLE 1

Summary of baseline characteristics of 26 patients with platinum-resistant recurrent ovarian cancer in the ongoing study

| Baseline characteristic | IN10018 + PLD (n = 26) | |
|---|---|---|
| | n | % |
| Age (years) | | |
| Median value (range) | 55 (41 to 73 years old) | |
| FIGO staging | | |
| III | 14 | 53.8% |
| IV | 12 | 46.2% |
| ECOG | | |
| 0 | 18 | 69.2% |
| 1 | 8 | 30.8% |
| Type of disease | | |
| Ovarian Cancer | 25 | 96.2% |
| Fallopian tube cancer | 1 | 3.8% |
| Tissue type | | |
| High-grade serous | 26 | 100.0% |
| Number of prior lines of systemic therapy | | |
| 1 | 18 | 69.2% |
| 2 | 7 | 26.9% |
| 3 | 1 | 3.8% |
| Prior bevacizumab use | 2 | 7.7% |

TABLE 2

Baseline characteristics of subjects - study IN10018-006
Baseline characteristics - patients with evaluable efficacy

| Subject number | Gender | Age | Tissue type | FIGO staging | ECOG | Previous treatment |
|---|---|---|---|---|---|---|
| 0860030001 | Female | 51 | High-grade serous | IIIC | 0 | First line: Docetaxel + carboplatin (6 cycle) |
| 0860030002 | Female | 44 | High-grade serous | IV | 0 | First line: Paclitaxel + carboplatin (8 cycle) |
| 0860030004 | Female | 57 | High-grade serous | IIIC | 0 | Neoadjuvant: Docetaxel + carboplatin (3 cycle); First line: Docetaxel + carboplatin (4 cycle) |
| 0860030005 | Female | 48 | High-grade serous | IV | 1 | First line: Docetaxel + cis-platinum (6 cycle); First-line maintenance: investigational drug (IMP4297, a PARP inhibitor) |
| 0860030006 | Female | 54 | High-grade serous | IIIC | 0 | First line: Paclitaxel + carboplatin (6 cycle) |
| 0860030007 | Female | 50 | High-grade serous | IV | 0 | First line: Paclitaxel + carboplatin (6 cycle); Platinum sensitive recurrence: Paclitaxel + carboplatin (6 cycle) |
| 0860030009 | Female | 57 | High-grade serous | IVA | 0 | Neoadjuvant: Paclitaxel + carboplatin (2 cycle); First line: Paclitaxel + carboplatin (5 cycle) |
| 0860030010 | Female | 62 | High-grade serous | IIIC | 0 | First line: Paclitaxel + carboplatin (8 cycle); Platinum sensitive recurrence: Paclitaxel + Lobaplatin (6 cycle) |
| 0860030011 | Female | 54 | High-grade serous | IVB | 0 | Neoadjuvant: Paclitaxel + carboplatin (3 cycle); First line: Paclitaxel + carboplatin (6 cycle); First-line maintenance: Olaparib (10 months); Platinum sensitive recurrence: Paclitaxel + cis-platinum (6 cycle); Maintenance: Niraparib (5 months) |
| 0860020002 | Female | 73 | High-grade serous | IVB | 1 | First line: Docetaxel + carboplatin (6 cycle) |
| 0860020003 | Female | 64 | High-grade serous | IIIC | 1 | Neoadjuvant: Docetaxel + carboplatin (1 cycle); First line: Docetaxel + carboplatin (4 cycle); Platinum sensitive recurrence: Docetaxel + carboplatin (8 cycle); Maintenance treatment: Olaparib (4 months). |

TABLE 2-continued

Baseline characteristics of subjects - study IN10018-006
Baseline characteristics - patients with evaluable efficacy

| Subject number | Gender | Age | Tissue type | FIGO staging | ECOG | Previous treatment |
|---|---|---|---|---|---|---|
| 0860020005 | Female | 55 | High-grade serous | IVB | 1 | First line: Docetaxel + Nedaplatin (7 cycle); Platinum sensitive recurrence: Docetaxel + carboplatin (5 cycle) |
| 0860010001 | Female | 60 | High-grade serous | IVB | 0 | First line: Paclitaxel + carboplatin (8 cycle) |
| 0860010002 | Female | 66 | High-grade serous | IV | 0 | First line: Paclitaxel + carboplatin (6 cycle) |
| 0860010003 | Female | 49 | High-grade serous | IIIC | 0 | First line: Paclitaxel + carboplatin (7 cycle) |
| 0860010004 | Female | 58 | High-grade serous | IIIB | 0 | First line: Paclitaxel + carboplatin (8 cycle) |
| 0860010005 | Female | 41 | High-grade serous | IIIC | 0 | First line: Docetaxel + carboplatin (6 cycle) |
| 0860070002 | Female | 48 | High-grade serous | IVB | 0 | Neoadjuvant: Paclitaxel + Lobaplatin (3 cycle); First line: Paclitaxel + cis-platinum (5 cycle); Platinum sensitive recurrence: Paclitaxel + cis-platinum + Bevacizumab (5 cycle) |

Efficacy

The study evaluated the change of tumor burden over time based on tumor imaging examination to evaluate the anti-tumor efficacy of IN10018 combined with PLD therapy in subjects with platinum-resistant ovarian cancer. Imaging examination by contrast-enhanced computed tomography (CT) was preferred for the study. For the abdomen and pelvis, contrast-enhanced magnetic resonance imaging (MRI) can be used when iodinated contrast CT is contraindicated. MRI was the examination of choice for brain imaging, with other imaging techniques, such as PET/CT and bone scans available if needed.

Imaging examinations during the screening period must be performed within 28 days prior to assignment of study treatment. During the study period, the subjects will receive tumor imaging examinations every 8 weeks (56±7 days), until the subjects are evaluated by the investigators to find the disease progression confirmed by imaging, start a new anti-tumor treatment, are withdrawn from the study or die (whichever occurs first).

The study will evaluate the efficacy on tumors according to Response Evaluation Criteria in Solid Tumors Version 1.1 (RECIST 1.1). Efficacy indicators include objective response rate (ORR), disease control rate (DCR), duration of response (DOR), progression-free survival (PFS) and overall survival (OS).

Among 18 efficacy-evaluable patients, 11 patients were observed for partial responses (PR), ORR was 61.1% (11/18), DCR was 88.9% (16/18), and 83.5% (15/18) of patients had reduction in tumor target lesions.

See Table 3, Table 4 and FIG. 1 for details.

TABLE 3

Summary of the best objective response

| Efficacy evaluation | Population with evaluable efficacy (N = 18) | |
|---|---|---|
| | N | % |
| Complete response (CR) | 0 | 0 |
| Partial response (PR) | 11 | 61.1 |
| Objective response rate (ORR) | 11 | 61.1 |
| Stable disease (SD) | 5 | 27.8 |
| Disease control rate (DCR) | 16 | 88.9 |
| Progression of disease (PD) | 2 | 11.1 |

TABLE 4

List of efficacy and changes in tumor target lesions with treatment

| Subject number | Baseline Time | Size | 1st examination Time | Size | 2nd examination Time | Size | 3rd examination Time |
|---|---|---|---|---|---|---|---|
| 0860030001 | 2020 Jul. 28 | 20.3 | 2020 Oct. 26 | 13.2 | — | — | — |
| 0860030002 | 2020 Aug. 1 | 36 | 2020 Nov. 16 | 23 | 2020 Dec. 15 | 23 | 2021 Jan. 14 |
| 0860030004 | 2020 Oct. 26 | 68 | 2021 Jan. 18 | 37 | 2021 Feb. 18 | 34 | 2021 Mar. 18 |
| 0860030005 | 2020 Oct. 20 | 16 | 2021 Jan. 26 | 15 | 2021 Mar. 24 | 12 | 2021 May 19 |
| 0860030006 | 2020 Dec. 1 | 17 | 2021 Feb. 2 | 13 | — | — | — |
| 0860030007 | 2020 Nov. 26 | 48 | 2021 Feb. 2 | 42 | 2021 Mar. 30 | 35 | 2021 May 26 |
| 0860030009 | 2021 Apr. 13 | 15 | 2021 Jun. 15 | 12 | 2021 Jul. 14 | 11 | 2021 Aug. 23 |
| 0860030010 | 2021 Apr. 22 | 39 | 2021 Jun. 21 | 32 | 2021 Aug. 18 | 25 | 2021 Sep. 16 |
| 0860030011 | 2021 May 7 | 44 | 2021 Jul. 5 | 59 | — | — | — |
| 0860020002 | 2020 Dec. 4 | 112.3 | 2021 Mar. 1 | 66.1 | 2021 Apr. 7 | 67.7 | 2021 May 25 |
| 0860020003 | 2021 Feb. 27 | 34.3 | 2021 Apr. 23 | 34.5 | 2021 May 5 | 35.6 | — |
| 0860020005 | 2021 Mar. 19 | 33.2 | 2021 May 19 | 24.4 | 2021 Jul. 15 | 16.3 | 2021 Aug. 18 |

TABLE 4-continued

List of efficacy and changes in tumor target lesions with treatment

| | | | | | | | | |
|---|---|---|---|---|---|---|---|---|
| 0860010001 | 2021 Feb. 26 | 12 | 2021 Apr. 28 | 8 | 2021 Jun. 28 | 5 | 2021 Aug. 20 | |
| 0860010002 | 2021 Mar. 10 | 50 | 2021 May 6 | 50 | 2021 Jul. 1 | 59 | — | |
| 0860010003 | 2021 Mar. 12 | 29.8 | 2021 May 10 | 28.8 | 2021 Jun. 15 | 29.7 | — | |
| 0860010004 | 2021 Mar. 31 | 36.3 | 2021 May 31 | 36.6 | 2021 Jul. 26 | 29.9 | 2021 Sep. 17 | |
| 0860010005 | 2021 Apr. 23 | 52.2 | 2021 Jun. 23 | 30.7 | 2021 Jul. 19 | 29.5 | 2021 Aug. 16 | |
| 0860070002 | 2021 May 25 | 85 | 2021 Jul. 16 | 84 | 2021 Aug. 16 | 81 | — | |

| Subject number | 3rd examination Size | 4th examination Time | Size | 5th examination Time | Size | Optimal efficacy | Optimal reduction |
|---|---|---|---|---|---|---|---|
| 0860030001 | — | — | — | — | — | PR | −35.0% |
| 0860030002 | 22 | 2021 Feb. 7 | 27 | — | — | PR | −38.9% |
| 0860030004 | 32 | 2021 May 14 | 42 | — | — | PR | −52.9% |
| 0860030005 | 10 | 2021 Jun. 21 | 10 | 2021 Jul. 21 | 8 | PR | −50.0% |
| 0860030006 | — | — | — | — | — | PD | −23.5% |
| 0860030007 | 28 | 2021 Jul. 15 | 27 | 2021 Aug. 11 | 23 | PR | −52.1% |
| 0860030009 | 10 | 2021 Oct. 15 | 10 | 2021 Dec. 29 | 8 | PR | −46.7% |
| 0860030010 | 22 | — | — | — | — | PR | −43.6% |
| 0860030011 | — | — | — | — | — | PD | 34.1% |
| 0860020002 | 67.2 | 2021 Jul. 26 | 71.4 | — | — | PR | −41.1% |
| 0860020003 | — | — | — | — | — | SD | 0.6% |
| 0860020005 | 18.6 | 2021 Sep. 15 | 22.5 | — | — | PR | −50.9% |
| 0860010001 | 4 | 2021 Oct. 18 | 3 | 2021 Dec. 10 | 2 | PR | −83.3% |
| 0860010002 | — | — | — | — | — | SD | 0.0% |
| 0860010003 | — | — | — | — | — | SD | −3.4% |
| 0860010004 | 29 | 2021 Nov. 15 | 30 | — | — | SD | −20.1% |
| 0860010005 | 28 | — | — | — | — | PR | −46.4% |
| 0860070002 | — | — | — | — | — | SD | −4.7% |

The best change in the total diameter of target lesions relative to the baseline=(the minimum total diameter of target lesions after treatment−the total diameter of baseline target lesions)/the total diameter of baseline target lesions× 100%

Safety

Phase Ib of the study includes a dose determination stage and a dose expansion stage. The main purpose of the dose determination stage is to determine the optimal dose of IN10018 combined with PLD treatment, i.e., the recommended phase 2 dose (RP2D) through safety assessment, such as dose-limiting toxicity.

A total of 9 subjects were enrolled in the dose determination stage of the study, among which the first 3 subjects received IN10018 100 mg combined with PLD 50 mg/m$^2$ (initial dose) treatment, and the last 6 subjects received IN10018 100 mg combined with PLD 40 mg/m$^2$ treatment.

Two of the 3 subjects who received IN10018 100 mg combined with PLD 50 mg/m$^2$ treatment reported 2 cases of dose-limiting toxicity (DLT): grade 4 neutropenia and grade 3 abdominal pain. Two of the first 3 subjects had DLT in the study of the initial dose, and these 2 DLTs were related to PLD and had nothing to do with IN10018 according to the investigator's assessment. Thus the study enrollment at the initial dose was stopped according to the protocol, and 6 additional subjects were enrolled at the lower dose (IN10018 100 mg combined with PLD 40 mg/m$^2$). No DLTs occurred during the first treatment cycle at this dose, so IN10018 100 mg combined with PLD 40 mg/m$^2$ was identified as RP2D for the combination therapy.

TABLE 5

Occurrence of dose-limiting toxicity (DLT) in different dose groups - study IN10018-006

| Subject number | Whether DLT occurred | DLT description |
|---|---|---|
| IN10018 100 mg QD + PLD 50 mg/m$^2$ Q4W | | |
| 0860030001 | No | None |
| 0860030002 | Yes | Grade 4 neutropenia (D15-D20, for 6 days); resulted in PLD decrement in cycle 2, consistent with the definition of DLT; judged by the investigator to be associated with PLD and not with IN10018 |
| 0860030003 | Yes | Grade 3 abdominal pain (D4-D8, for 5 days), consistent with the definition of DLT; judged by the investigator to be associated with PLD and not with IN10018 |
| IN10018 100 mg QD + PLD 40 mg/m$^2$ Q4W | | |
| 0860030004 | No | None |
| 0860030005 | No | None |
| 0860020002 | No | None |
| 0860030006 | No | None |
| 0860030007 | No | None |
| 0860010001 | No | None |

DLT refers to the dose-limiting toxicity specified in the protocol that occurs in the first treatment cycle.

By Jun. 22, 2021, 21 of the 22 subjects enrolled had adverse events (AEs), and according to the investigator's assessment, 20 of them had AEs related to IN10018. Regardless of the correlation, the system organ classes (SOC) of AE reported by at least 2 subjects were investigations (90.9%), gastrointestinal disorders (81.8%), renal and urinary disorders (72.7%), general disorders and administration site conditions (59.1%), metabolism and nutrition disorders (59.1%), infections and infestations (54.5%), blood and lymphatic system disorders (50.0%), respiratory, thoracic and mediastinal disorders (27.3%), musculoskeletal and connective tissue disorders (22.7%), skin and subcutaneous tissue disorders (18.2%), nervous system disorders (13.6%), cardiac disorders (18.2%) and psychiatric disorders (9.1%). IN10018-related AEs reported by at least 2 subjects included proteinuria (68.2%), nausea (54.5%), vomiting (40.9%), fatigue (31.8%), loss of appetite (27.3%), diarrhea (22.7%), anemia (27.3%), hypoalbuminemia (18.2%), elevated aspartate aminotransferase (18.2%), decreased body weight (13.6%), decreased lymphocyte count (13.6%), discomfort (13.6%), hematuria (13.6%), hypokalemia (9.1%), decreased neutrophil count (9.1%), elevated total bile acid (9.1%), hypercholesterolemia (9.1%) and peripheral edema (9.1%). All proteinuria was grade 1 or 2, reversible without changes in renal function. Except for 1 subject who reported proteinuria as an adverse event of special interest (CTCAE grade 2) and resulted in discontinuation of IN10018 administration, all proteinuria resolved spontaneously without need to adjust the dose of IN10018. Most of the adverse events related to IN10018 were CTCAE grade 1 or 2, and no CTCAE grade 4 and 5 drug-related adverse events were reported. Common drug-related adverse events listed by highest CTCAE grade and preferred terms are shown in Table 6 below.

By Jun. 22, 2021, a total of 5 of the 22 subjects enrolled had serious adverse events (SAEs), of which 3 subjects reported SAEs related to IN10018: loss of appetite (grade 3, related to both IN10018 and PLD), constipation (grade 2, related to both IN10018 and PLD), abdominal distension (grade 3, related to both IN10018 and PLD), and elevated creatinine (grade 2, related to both IN10018 and PLD). No subject had adverse events leading to dose reduction of IN10018. Adverse events leading to discontinuation of study treatment were reported by 2 subjects, wherein loss of appetite (grade 3) leading to discontinuation in 1 subject was associated with both IN10018 and PLD. One subject reported septic shock leading to death, which was not related to study treatment according to the investigator's assessment. There were no adverse events leading to death in the study. No significant abnormal trends in laboratory examination values were observed.

The contents of all references (including literature references, issued patents, published patent applications, and co-pending patent applications) cited throughout this application are expressly incorporated herein by reference in their entirety. Unless otherwise defined, all technical and scientific terms used herein have the same meaning as commonly known to those skilled in the art.

All features disclosed in this specification may be combined in any combination. Each feature disclosed in this specification may be replaced by alternative features serving the same, equivalent or similar purpose. Thus, unless expressly stated otherwise, each feature disclosed is only an example of a series of equivalent or similar features.

From the above description, one skilled in the art can easily ascertain the essential characteristics of this invention, and can make various changes and modifications of the invention without departing from the spirit and scope of the invention to adapt them to various usages and conditions. Accordingly, other embodiments are also within the scope of the appended claims.

TABLE 6

Frequency of adverse events related to IN10018 reported by at least 3 subjects shown according to highest CTCAE grade and preferred terms - study IN10018-006

| AE | Grade 1 N (%) | Grade 2 N (%) | Grade 3 N (%) | Grade 4 N (%) | Grade 5 N (%) | All grades N (%) |
|---|---|---|---|---|---|---|
| Subject | 22 | 22 | 22 | 22 | 22 | 22 (100) |
| Subjects having drug-related AE | 20 (90.9) | 12 (54.5) | 1 (4.5) | 0 | 0 | 20 (90.9) |
| Proteinuria | 10 (45.5) | 5 (22.7) | 0 | 0 | 0 | 15 (68.2) |
| Nausea | 10 (45.5) | 2 (9.1) | 0 | 0 | 0 | 12 (54.5) |
| Vomiting | 8 (36.4) | 1 (4.5) | | | | 9 (40.9) |
| Fatigue | 7 (31.8) | 0 | 0 | 0 | 0 | 7 (31.8) |
| Loss of appetite | 5 (22.7) | 0 | 1 (4.5) | 0 | 0 | 6 (27.3) |
| Anemia | 4 (18.2) | 2 (9.1) | 0 | 0 | 0 | 6 (27.3) |
| Diarrhea | 5 (22.7) | 0 | 0 | 0 | 0 | 5 (22.7) |
| Elevated AST | 4 (18.2) | 0 | 0 | 0 | 0 | 4 (18.2) |
| Hypoalbuminemia | 4 (18.2) | 0 | 0 | 0 | 0 | 4 (18.2) |
| Decreased body weight | 3 (13.6) | 0 | 0 | 0 | 0 | 3 (13.6) |
| Decreased lymphocyte count | 2 (9.1) | 2 (9.1) | 0 | 0 | 0 | 3 (13.6) |
| Hematuria | 3 (13.6) | | | | | 3 (13.6) |
| Discomfort | 1 (4.5) | 2 (9.1) | | | | 3 (13.6) |

What is claimed is:

1. A method of treating ovarian cancer, the method comprising administering to a subject in need thereof a therapeutically effective amount of therapeutic agent (a) and therapeutic agent (b), wherein:

the therapeutic agent (a) is the compound of formula (I) or a pharmaceutically acceptable salt thereof

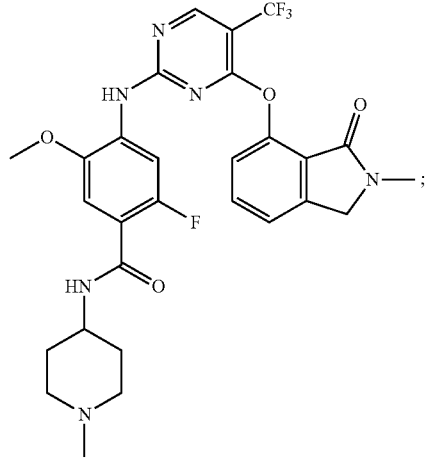

the therapeutic agent (b) is PLD or a pharmaceutically acceptable salt thereof;
the compound of formula (I) or a pharmaceutically acceptable salt thereof is administered at a dose of 10 mg/day to 300 mg/day in an adult, and the dose is calculated based on free base.

2. The method of claim 1, wherein the therapeutic agent (a) and the therapeutic agent (b) are administered simultaneously, separately or sequentially.

3. The method of claim 1, wherein the compound of formula (I) or a pharmaceutically acceptable salt thereof is administered at a dose of 100 mg/day in an adult, and the dose is calculated based on free base.

4. The method of claim 1, wherein the PLD or a pharmaceutically acceptable salt thereof is administered at a dose of 20 to 40 mg/m² per week in an adult, and the dose is calculated based on PLD.

5. The method of claim 4, wherein the PLD or a pharmaceutically acceptable salt thereof is administered at a dose of 40 mg/m² per week in an adult, and the dose is calculated based on PLD.

6. The method of claim 1, wherein the pharmaceutically acceptable salt of the compound of formula (I) is tartrate.

7. The method of claim 1, wherein the compound of formula (I) or a pharmaceutically acceptable salt thereof is administered daily, and PLD or a pharmaceutically acceptable salt thereof is administered once a week, every 4 weeks (28 days) as a cycle.

8. The method of claim 1, wherein the ovarian cancer is ovarian epithelial cancer.

9. The method of claim 8, wherein the ovarian epithelial cancer is recurrent ovarian epithelial cancer.

10. A combination formulation comprising:
(a) a unit dosage form of one or more compounds each having the structure of formula (I) or a pharmaceutically acceptable salt thereof, and
(b) a unit dosage form of one or more PLDs or pharmaceutically acceptable salts thereof,

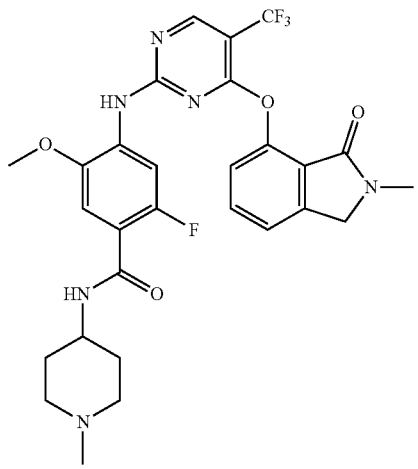

for the treatment of ovarian cancer.

11. The combination formulation of claim 10, wherein the ovarian cancer is ovarian epithelial cancer.

12. The combination formulation of claim 11, wherein the ovarian epithelial cancer is recurrent ovarian epithelial cancer.

13. The method of claim 1, wherein the compound of formula (I) or a pharmaceutically acceptable salt thereof is administered at a dose of 50 mg/day to 150 mg/day in an adult, and the dose is calculated based on free base.

14. The method of claim 13, wherein the compound of formula (I) or a pharmaceutically acceptable salt thereof is administered at a dose of 25 mg/day to 200 mg/day in an adult, and the dose is calculated based on free base.

15. The method of claim 9, wherein the recurrent ovarian epithelial cancer is platinum-resistant recurrent ovarian epithelial cancer or platinum-sensitive recurrent ovarian epithelial cancer.

16. The method of claim 15, wherein the recurrent ovarian epithelial cancer is platinum-resistant recurrent ovarian epithelial cancer.

17. The combination formulation of claim 12, wherein the recurrent ovarian epithelial cancer is platinum-resistant recurrent ovarian epithelial cancer or platinum-sensitive recurrent ovarian epithelial cancer.

18. The combination formulation of claim 17, wherein the recurrent ovarian epithelial cancer is platinum-resistant recurrent ovarian epithelial cancer.

* * * * *